United States Patent [19]

Krzewki et al.

[11] Patent Number: 5,342,619
[45] Date of Patent: Aug. 30, 1994

[54] POLYURETHANE INSECTICIDAL EAR TAG, METHODS OF USE AND PREPARATION

[75] Inventors: Rudolf J. Krzewki, St. Joseph; Stanley Ackers, Kansas City, both of Mo.

[73] Assignee: Fermenta Animal Health Company, Kansas City, Mo.

[21] Appl. No.: 24,905

[22] Filed: Mar. 2, 1993

Related U.S. Application Data

[63] Continuation of Ser. No. 841,836, Feb. 26, 1992, abandoned.

[51] Int. Cl.$^5$ ............................................. A01N 25/10
[52] U.S. Cl. ................................. 424/411; 424/405; 424/419; 424/DIG. 10; 514/919; 523/103
[58] Field of Search ............... 424/405, 411, 419, 403; 523/103, 122, 163, 167; 524/130, 131, 132; 528/51

[56] References Cited

U.S. PATENT DOCUMENTS 4,189,467  2/1980  von Bittera et al. ............... 424/411
4,380,598  4/1983  Robeson ............................ 524/163

FOREIGN PATENT DOCUMENTS 2111830  12/1981  United Kingdom ............... 424/411

*Primary Examiner*—Thurman K. Page
*Assistant Examiner*—Neil Levy
*Attorney, Agent, or Firm*—Shook, Hardy & Bacon

[57] ABSTRACT

A polymeric device and method for the control of insects on animals is disclosed. The device is in the form of an ear tag or other shape which can be attached to an animal using known techniques. A unique polymer/insecticidal formulation is provided by combining an ectoparasiticidal active compound, preferably an organophosphate, with a polyurethane polymer. The polymer is the reaction product of 4,4'-diphenylmethane diisocyanate, polytetramethylene glycol and 1,4-butanediol. By utilizing the particular polymers described, high loadings of insecticides are possible and the resulting product shows no tendency to exude insecticide during prolonged storage. The product made according to the invention can provide effective control of horn flies on cattle for six months or more utilizing a single ear tag or the like where it would take two tags constructed according to the prior art to achieve comparable results. The result is lower costs in product and labor, greater safety to an animal and workers and a lower quantity of residual product to dispose.

14 Claims, No Drawings

POLYURETHANE INSECTICIDAL EAR TAG, METHODS OF USE AND PREPARATION

This is a continuation of copending application(s) Ser. No. 07/841,836 filed on Feb. 26, 1992, now abandoned.

This invention relates generally to insecticidal protective tags for non-human domestic animals and, in particular, to a tag formed from a polyurethane polymer having an ectoparasiticidal active compound within the polymer matrix.

BACKGROUND OF THE INVENTION

It has long been known that ear tags impregnated with insecticide are an effective means for providing control of horn flies and other insects on domestic livestock, particularly cattle. The most common material for formulating insecticidal animal tags has heretofore been polyvinyl chloride. In recent years, concern from ecological and human safety viewpoints have been raised with regard to utilizing plasticized polyvinyl chloride on animals intended for human consumption. Also, since polyvinyl chloride must be plasticized to perform satisfactorily as a tag, the quantity of active insecticide which can be incorporated into the product is reduced in direct proportion to the quantity of plasticizer required.

Another disadvantage of present insecticidal tag formulating techniques is that the high loadings of plasticizer and insecticide cause the completed product to "bleed" (exude) insecticide. This makes an unacceptable commercial product which requires special packaging to accommodate a relatively long shelf life, necessitates avoiding high temperatures in transport and storage, and demands special handling requirements when the product is removed from the package for application to an animal.

It has also been previously known to utilize polyurethane resins for forming identification (I.D.) tags for animals. It is also known to use polyurethane I.D. tags and attach to same a porous or semi-permeable membrane in the form of a cell for holding a reservoir of insecticide. These membranes are made of a variety of different polymers including polyurethane. Their construction is shown and described in U.S. Pat. No. 4,562,794. The purported advantage to utilizing such a membrane is to provide greater control over the uniformity of release rate of the insecticide and higher insecticide depletion than can be obtained when the insecticide is within the polymer matrix. Some of the polymer which have heretofore been utilized for tags of the type contemplated by the referenced patent would not, however, permit sufficiently high loadings of insecticide to achieve a satisfactory tag by blending directly with an ectoparasiticidal compound. Inherently, this known construction is costly to manufacture because of the complicated steps of forming and filling the cell as well as making the mechanical fastener for joining the cell to the tag. Also, there is a higher than desirable incidence of product failure because of the membranes being punctured while in use on animals.

The polyurethane resins which are useful in the present invention are polyurethane aromatic polyether elastomers, specifically the polymers which are the reaction product of 4,4'-diphenylmethane diisocyanate, polytetramethylene glycol and 1,4-butanediol. These resins generally conform to Chemical Abstracts Service Registry Number CAS 9018-04-6.

OBJECTS AND SUMMARY OF THE PRESENT INVENTION

It is therefore an object of the present invention to provide an insecticidal animal protective tag which will accommodate a higher degree of loading of the insecticidal compound than previously known tags, thereby enhancing the effectiveness of the tag and extending its useful life.

Another objective of this invention is to provide an insecticidal animal protective tag and method of preparing same which minimizes insecticide bleeding, thereby improving the shelf life of the product while reducing the risk of contamination by humans handling the ear tags.

Another one of the objectives of this invention is to minimize environmental and health concerns regarding insecticidal tag devices by utilizing a polymeric matrix which is generally recognized as being environmentally safe and non-threatening to humans and does not require the addition of potentially dangerous plasticizers.

It is also an object of this invention to provide a method of protecting animals from insects, which is more environmentally safe and presents fewer health risks than existing practices.

As a corollary to the foregoing object, it is an important aim of this invention to provide an insecticide ear tag which is as effective as two prior art tags using the same active compound.

These and other objects of the invention will be made clear or become apparent from the following specification and claims.

The foregoing objects are achieved by an insecticidal tag-like device comprising an ectoparasiticidal active compound, preferably an organophosphate, that is blended with a polymer which is the reaction product of 4,4'-diphenylmethane diisocyanate, polytetramethylene glycol and 1,4-butanediol. The invention also encompasses a method of preparing such a device by combining the ectoparasiticidal composition with the afore-described polymer.

Lastly, the invention encompasses a method of protecting non-human domestic animals from ectoparasites by attaching to the animal a device, such as an ear tag, formed from a polymer which is the reaction product of 4,4'-diphenylmethane diisocyanate, polytetramethylene glycol and 1,4-butanediol, the ectoparasiticidal active compound preferably being an organophosphate present in a quantity of up to 70% by weight of the total weight of the article.

DETAILED DESCRIPTION OF THE INVENTION

The polymers useful in this invention are formed by polymerization of the diisocyanate with glycol according to the following reactions:

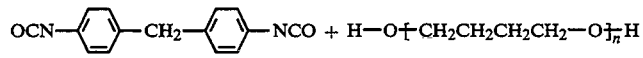

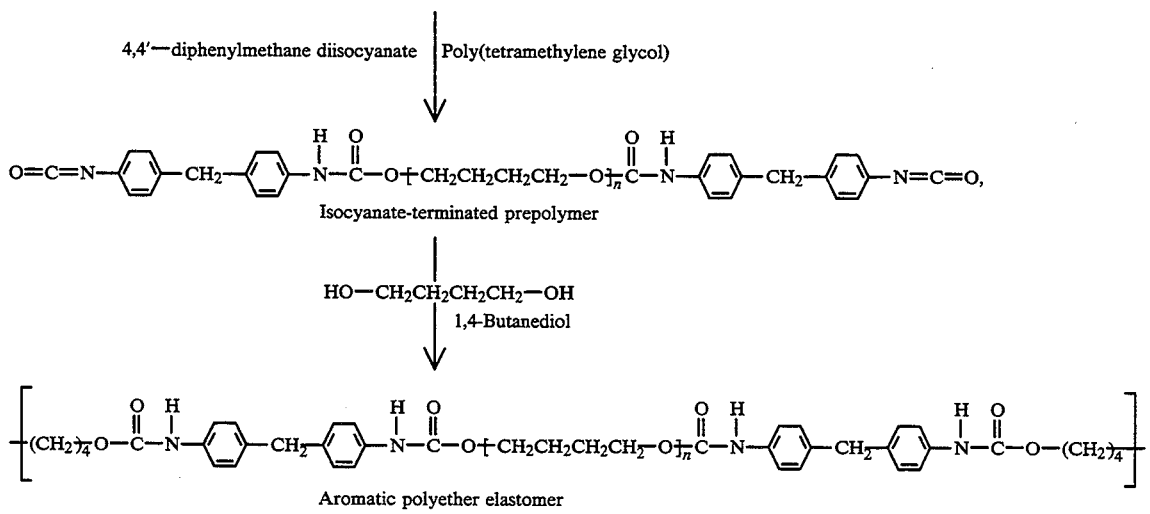

the moieties of the polymerization reaction will generally be present within the ranges of 20% to 40% diisocyanate, 50% to 70% glycol, and 2% to 10% butanediol (all by weight). It should be understood that the invention is not limited to ear tags and could take the form of a tail tag, ear clip, leg bracelet, collar, horse strip, medallion, chain tag or other device which could be attached to an animal, The final polymer will have a Shore hardness of 70–90 A units, a number average molecular weight which is not less than about 90000, and a melting range within about 70° C. to 190° C. The following commercial resin products, all meeting the foregoing criteria, have been confirmed as satisfying the objectives of the invention and will be referred to hereinafter by the reference letters A through F:

| Reference Letter | Trademark | Manufacturer |
| --- | --- | --- |
| A | Texin 985 A | Mobay Chemical Pittsburgh, PA USA |
| B | Morthane PE-90 | Morton Thiokol, Inc. Chicago, IL USA |
| C | Estane 98315 | B. F. Goodrich Co. Cleveland, OH USA |
| D | Morthane PE-50 | Morton Thiokol, Inc. Chicago, IL USA |
| E | Elastollan 1180A | BASF Corp. Parsippany, NJ USA |
| F | Pellethane 2103-80 | Dow Chemical Midland, MI USA |

Various insecticidal compositions, both liquids and solids, can be employed although preferably an ectoparasiticidal active compound which is an organophosphate will be the active component. Suitable insecticides include O,O-diethyl-O-2-isopropyl-6-methyl-6-pyrimidin-4-yl phosphorothioate, sold under the trademark Diazinon (Ciba-Geigy), S-[1,2-bis(ethoxycarbonyl) ethyl]0,O-dimethyl phosphorodithioate, commonly known as malathion, 0,0-dimethyl-0-4-nitro-m-tolyl phosphorothioate, sold under the trademark Sumithion by Sumitomo Chemical Co. Ltd, and 0,0,0',0'-tetraethyl-S,S'-methylene bis(phosphorodithioate), commonly known as ethion and sold by FMC, Inc.

The ectoparasiticidal active compound should be present in an ectoparasiticidal effective quantity, normally at least approximately 20% by weight (based on final product) with levels up to approximately 70% by weight being acceptable. Thus, the polymer component will be present from 30% to 80% by weight of the final product. The ectoparasiticidal active compound, if liquid, may be introduced into the resin by a heating, absorption process, or if solid, it may first be dissolved in a volatile solvent followed by soaking in the polymer and removal of the solvent. Generally a blending time of thirty minutes in a high intensity mixer will produce a homogeneous, free flowing, polymer/insecticide mixture (called a "dry blend").

It is, of course, to be understood that ultraviolet light stabilizers such as 2-(2'-hydroxy-5'-methyl phenyl)-benzotriazole, fillers, lubricants, dyes, antioxidants such as octadecyl 3,5-di-tert-butyl-4-hydroxy-hydrocinnamate, pigments, and other inert ingredients may be incorporated into the formulation from zero to 2% by weight of the final product for serving their accepted functions which are well known to those skilled in the art. It has been found preferable to utilize up to 20% by weight polyvinyl chloride as a processing component to facilitate production of a free flowing dry blend. All of the foregoing optional substituents are generally added after the insecticide has been absorbed into the polymer. High intensity mixing for approximately five minutes is adequate to provide a homogeneous mixture incorporating the optional components.

The previously compounded dry blend may be formed into an acceptable shape, such as an ear tag, for attaching to an animal by various techniques well known to those skilled in the art. Extrusion, injection, and compression molding are all well known techniques, with injection molding being the preferred method of forming the preferred form of the device, namely, ear tags.

A preferred range for polymer and insecticide is 40% to 60% by weight polymer and 30% to 60% ectoparasiticidal active compound with the balance comprising polyvinyl chloride (up to 20% by weight) and up to 2% by weight inert ingredients such as antioxidants, ultraviolet light stabilizers and pigments, all well known to those skilled in the art (all weight percents based on final product).

The following examples are illustrative of some of the possible variations which are contemplated as being within the scope of the invention.

EXAMPLE 1

Various polymer compositions incorporating Diazinon insecticide were prepared according to the absorption procedure previously described utilizing technical grade (88% purity by weight) Diazinon and quantities within the preferred range. Ear tags were formed from the dry blend by injection molding.

Table I summarizes the composition formulations of the ear tags made according to this example.

TABLE I

Polyurethane Tags Made With Varying Quantities of Resin C and Insecticide

| Lot No. (minimum 200 tags) | Composition, wt. % | | | | | |
|---|---|---|---|---|---|---|
| | 1 | 2 | 3 | 4 | 5 | 6 |
| Resin C | 49.4 | 51.3 | 50.8 | 48.8 | 52.6 | 48.5 |
| Diazinon (88%) | 38.3 | 46.1 | 43.1 | 43.9 | 46.0 | 43.7 |
| PVC | 12.3 | 2.6 | 5.1 | 6.1 | 0 | 6.0 |
| UV and antioxidant Stabilizers (approx. 1:1 by weight) | — | — | — | 0.7 | 0.8 | 1.0 |
| Colorants, Pigments | — | — | 1.0 | 0.5 | 0.6 | 0.8 |
| Average Tag Weight (g) | 14.69 | 14.43 | 14.56 | 14.00 | 15.83 | 13.88 |

Table II provides a summary of the insecticide released during field trials utilizing the tags identified in Table I.

TABLE II

Field Trials
Average Release Rate of Diazinon
For Tags From Table I

| Lot No. | 1 | | 2 | | 3 | | 4 | | | 5 | 6 |
|---|---|---|---|---|---|---|---|---|---|---|---|
| Location | #1 | #2 | #1 | #3 | #2 | #1 | #1 | #4 | #2 | #3 | #1 | #1 |
| Application Date | 1-9-90 | 5-15-90 | 1-20-90 | 3-30-90 | 5-15-90 | 3-30-90 | 3-30-90 | 5-17-90 | 6-27-90 | 7-26-90 | 11-12-90 | 11-15-90 |
| Removal Date | 7-20-90 | 10-11-90 | 7-28-90 | 8-29-90 | 11-26-90 | 9-14-90 | 10-20-90 | 10-3-90 | 10-30-90 | 11-11-90 | 3-30-91 | 4-3-91 |
| Days on Cattle | 191 | 149 | 189 | 151 | 196 | 168 | 204 | 140 | 126 | 108 | 137 | 138 |
| Total Diazinon Released (g) | 2.757 | 3.604 | 4.162 | 4.359 | 4.259 | 4.083 | 3.812 | 3.920 | 3.289 | 2.696 | 3.191 | 2.471 |
| Average Release Rate mg/day | 14.4 | 24.2 | 22.0 | 28.9 | 21.7 | 24.3 | 18.7 | 28.0 | 26.1 | 25.0 | 23.3 | 17.9 |

EXAMPLE 2

Various polymer compositions incorporating Diazinon insecticide were prepared according to the absorption procedure using technical grade (88% pure by weight) Diazinon and a dry blend was obtained. Ear tags were formed by injection molding. Table III summarizes the composition formulations of ear tags made according to this example and Table IV provides release rate data on these same tags.

TABLE III

Polyurethane Tags Made With Varying Quantities of Resins B, D, and F and Insecticide

| Log No. (minimum 200 tags) | Composition, wt. % | | | | |
|---|---|---|---|---|---|
| | 1 | 2 | 3 | 4 | 5 |
| Resin D | 53.9 | 42.4 | 51.7 | — | — |
| Resin B | — | — | — | 48.8 | — |
| Resin F | — | — | — | — | 48.4 |
| Diazinon (88%) | 45.8 | 57.3 | 46.5 | 43.9 | 43.5 |
| PVC | — | — | — | 6.1 | 6.0 |
| Stabilizers | — | — | 0.7 | 0.7 | 1.0 |
| Colorants, Pigments | 0.3 | 0.3 | 1.1 | 0.5 | 1.1 |
| Average Tag Weight (g) | 14.28 | 14.31 | 13.64 | 13.87 | 13.85 |

TABLE IV

Field Trials
Average Release Rate Of Diazinon
For Tags From Table III

| Lot No. | 1 | | 2 | | 3 | | | 4 | | | 5 |
|---|---|---|---|---|---|---|---|---|---|---|---|
| Location | #1 | #1 | #2 | #3 | #3 | #2 | #3 | #2 | #3 | #4 | #2 | #1 |
| Application Date | 3-31-90 | 3-30-90 | 3-23-90 | 5-15-90 | 5-15-90 | 3-27-90 | 6-27-90 | 7-26-90 | 6-27-90 | 5-25-90 | 6-23-90 | 11-10-90 |
| Removal Date | 7-21-90 | 9-15-90 | 8-29-90 | 10-31-90 | 10-1-90 | 8-29-90 | 10-30-90 | 11-11-90 | 10-30-90 | 10-29-90 | 12-01-90 | 4-01-90 |
| Days on Cattle | 112 | 169 | 159 | 168 | 140 | 155 | 126 | 108 | 126 | 157 | 161 | 141 |
| Total Diazinon Released (g) | 2.393 | 3.177 | 3.383 | 3.308 | 4.860 | 4.730 | 2.758 | 2.807 | 3.327 | 4.067 | 4.061 | 2.252 |
| Average Release Rate mg/day | 21.4 | 18.8 | 21.3 | 19.7 | 34.7 | 30.5 | 21.9 | 26.0 | 26.4 | 25.9 | 25.2 | 16.0 |

EXAMPLE 3

Ear tags from Lot 4 of Example 1 (Tables I and II) and from Lot 2 of Example 2 (Tables III and IV) were attached to the ears of cattle in herds located in New Mexico and Texas. One tag per animal was used to determine the efficacy against horn flies. In both trials, an untreated cattle herd was located within the vicinity of the tagged herd. On the application day, and weekly thereafter, horn fly counts were taken on at least ten randomly selected tagged and untagged animals. The results are summarized in Table V.

From this data it is evident that a surprising long term efficacy can be achieved with only one tag of the present composition, even under very high fly populations (infestation) for a period of at least six months.

TABLE V

Efficacy Trials - Control of Horn Flies
Lot 4, Example 1; Lot 2, Example 2

| Location: | #1 | | | #2 | | |
|---|---|---|---|---|---|---|
| Treatment Date: | 5-17-90 | | | 4-7-90 | | |
| | Average # of Flies per animal | | | Average # of Flies per animal | | |
| | Lot 4 Ex. 1 | Untagged Control | % Reduction | Lot 2 Ex. 2 | Untagged Control | % Reduction |
| # of Animals | 22 | 50 | | | | |
| | 35 | 50 | | | | |
| Pretreatment Count | 268 | 440 | | 800 | 800 | |
| # of Weeks | | | | | | |
| 1 | 22 | 498 | 96 | 90 | 800 | 89 |
| 2 | 14 | 484 | 97 | 150 | 800 | 81 |
| 3 | 4 | 668 | 99 | 100 | 900 | 89 |
| 4 | 5 | 630 | 99 | 20 | 750 | 97 |
| 5 | 9 | 618 | 99 | 12 | 500 | 98 |
| 6 | 4 | 396 | 99 | 10 | 500 | 98 |
| 7 | 3 | 452 | 99 | 10 | 400 | 98 |
| 8 | 6 | 602 | 99 | 6 | 300 | 98 |
| 9 | 30 | 750 | 96 | 10 | 200 | 95 |
| 10 | 26 | 1126 | 98 | 5 | 200 | 98 |
| 11 | 20 | 1166 | 98 | 6 | 200 | 97 |
| 12 | 22 | 1384 | 98 | 7 | 250 | 97 |
| 13 | 48 | 1038 | 95 | — | — | 97 |
| 14 | 64 | 984 | 93 | 20 | 250 | 92 |
| 15 | 38 | 1420 | 97 | 30 | 300 | 90 |
| 16 | 34 | 1106 | 97 | 10 | 300 | 97 |
| 17 | 5 | 706 | 99 | 40 | 300 | 87 |
| 18 | 24 | 594 | 96 | 14 | 350 | 96 |
| 19 | 36 | 610 | 94 | 20 | 300 | 93 |
| 20 | 164 | 540 | 70 | 30 | 300 | 90 |
| 21 | | | | 20 | 300 | 93 |
| 22 | | | | 25 | 300 | 92 |
| 23 | | | | 35 | 300 | 88 |
| 24 | | | | 30 | 200 | 85 |
| 25 | | | | 24 | 250 | 90 |

EXAMPLE 4

Ear tags containing 46 wt. % of a polyurethane resin, 46 wt. % of technical grade Diazinon, 6 wt. % of PVC resin and 2 wt. % total of stabilizers, dyes, and pigments were prepared using the following resins previously identified:

| Tag Lot No. | Resin |
|---|---|
| 1 | A |
| 2 | B |
| 3 | C |
| 4 | D |
| 5 | E |
| 6 | F |

An efficacy trial with all tags was conducted in Alabama. As in Example 3, only one tag per animal head was employed, and an untagged control herd was kept in the vicinity of the tagged herds. An average number of horn flies from at least ten randomly selected animals in each herd, taken on the application date and every two weeks thereafter, are listed in Table VI.

TABLE VI

Efficacy Trials - Control of Horn Flies
Average Number of Horn Flies Per Animal

| Lot No. | 1 | 2 | 3 | 4 | 5 | 6 | Untagged Control |
|---|---|---|---|---|---|---|---|
| # of Animals | 30 | 32 | 63 | 40 | 40 | 35 | 25 |
| Pretreatment Fly Count treatment date | 156 | 162 | 167 | 151 | 148 | 141 | 156 |

TABLE VI-continued

Efficacy Trials - Control of Horn Flies
Average Number of Horn Flies Per Animal

| Lot No. | 1 | 2 | 3 | 4 | 5 | 6 | Untagged Control |
|---|---|---|---|---|---|---|---|
| 4-25-91 # of Weeks | | | Post Treatment Count | | | | |
| 2 | 4.1 | 0.0 | 0.4 | 11.0 | 3.4 | 11.0 | 189 |
| 4 | 1.1 | 2.5 | 0.0 | 9.0 | 0.0 | 6.9 | 240 |
| 6 | 0.3 | 0.0 | 0.1 | 5.0 | 0.0 | 2.8 | 289 |
| 8 | 0.2 | 0.0 | 0.0 | 0.0 | 0.0 | 0.0 | 278 |
| 10 | 0.6 | 0.2 | 2.4 | 0.6 | 0.7 | 2.3 | 243 |
| 12 | 0.3 | 0.0 | 0.1 | 2.6 | 0.0 | 8.6 | 254 |
| 15 | 1.1 | 0.0 | 0.0 | 0.1 | 0.1 | 14.0 | 270 |
| 17 | 3.9 | 0.2 | 2.1 | 13.0 | 2.6 | 57.0 | 270 |

The method of preparing a device for protecting animals from insects according to the present invention comprises combining an ectoparasiticidal active compound with a polymer which is the reaction product of 4,4'-diphenylmethane diisocyanate, polytetramethylene glycol and 1,4-butanediol, and then forming the combination into a device which is attachable to an animal, such as an ear tag. The resin and ectoparasiticidal compound are preferably combined by utilizing 30% to 80% by weight polymer and 20% to 70% by weight of the compound. The most preferred method utilizes approximately 30% to 60% by weight of the ectoparasiticidal compound, 40% to 60% by weight polymer, and up to about 20% by weight polyvinyl chloride with up to 2% by weight inert ingredients, such as anti-oxidants, UV stabilizers, and pigment.

Lastly, the invention encompasses a method of protecting non-human domestic animals from ectoparasites which comprises attaching to the animal a device formed from a polymer which is the reaction product of 4,4'-diphenylmethane diisocyanate, polytetramethylene glycol and 1,4-butanediol, which polymer has been mixed with up to 70% by weight of an ectoparasiticidal active compound. The preferred method utilizes the percent by weight ranges previously specified for the method of preparing the device according to the invention. All percentages are by weight based on the final product.

From the foregoing it is apparent that the device and methods of the present invention provide for a highly effective way of protecting domestic animals from insects such as horn flies for a prolonged period of time. The devices according to the present invention are able to support surprisingly high loadings of organophosphate insecticides. Equally surprising is the fact that the devices remain dry without exudation of insecticide, even after prolonged storage at elevated temperatures. Also, notwithstanding the unusually high loading of insecticide, the tags remain flexible and strong for long retention on the animals being protected.

Having thus described the invention, what we claim is:

1. A device for protecting animals from insects, said device comprising:
   20% to 70% by weight of an ectoparasiticidal active organophosphate compound; and
   30% to 80% by weight of a quantity of a polymer which is the reaction product of 20% to 40% by weight 4,4'-diphenylmethane diisocyanate, 50% to 70% by weight polytetramethylene glycol and 2% to 10% by weight 1,4-butanediol,
   wherein said reaction product has a number average molecular weight of not less than about 90,000.

2. The device as set forth in claim 1, wherein said polymer has a Shore hardness of 70–90 A units.

3. The device as set forth in claim 1, wherein the ectoparasiticidal active organophosphate compound is present in an amount of 30% to 60% by weight and the polymer is present in an amount of 40% to 60% by weight.

4. The device as set forth in claim 3, including polyvinyl chloride in an amount up to 20% by weight.

5. A device for protecting animals from insects, said device comprising:
   30% to 50% by weight of an ectoparasiticidal active organophosphate compound; and
   40% to 60% by weight of a quantity of a polymer which has a number average molecular weight of not less than about 90,000 and is the reaction product of 20% to 40% by weight 4,4'-diphenylmethane diisocyanate, 50% to 70% by weight polytetramethylene glycol and 2 to 10% by weight 1,4-butanediol.

6. The device as set forth in claim 5, wherein is included up to 20% by weight polyvinyl chloride.

7. The device as set forth in claim 5, comprising 46% by weight polymer, 6% by weight polyvinyl chloride and 2% by weight inert ingredients.

8. The device as set forth in claim 5, wherein said polymer has a Shore hardness of 70–90 A units.

9. A method of preparing a device for protecting animals from insects, said method comprising the steps of
   combining 20% to 70% by weight of an ectoparasiticidal active organophosphate compound with 30% to 80% by weight of a polymer which has a number average molecular weight of not less than about 90,000 and comprises the reaction product of 20% to 40% by weight 4,4'-diphenylmethane diisocyanate, 50% to 70% by weight polytetramethylene glycol and 2% to 10% by weight 1,4-butanediol, and forming the combination into a device which is attachable to an animal.

10. The method as set forth in claim 9, wherein said combining step includes combining up to 20% by weight polyvinyl chloride.

11. The method as set forth in claim 9, wherein said combining step comprises combining 40% to 60% by weight of said polymer with 30% to 50% by weight of said compound.

12. The method as set forth in claim 9, wherein said combining step comprises combining 46% by weight of said polymer, 46% by weight of said compound, 6% by weight of polyvinyl chloride and 2% by weight inert ingredients.

13. A method of protecting non-human domestic animals from ectoparasites, said method comprising the steps of:
    attaching to the animal a device formed from a polymer which has a number average molecular weight of not less than about 90,000 and is the reaction product of 20% to 40% by weight 4,4'-diphenylmethane diisocyanate, 50% to 70% by weight polytetramethylene glycol and 2% to 10% by weight 1,4-butanediol, which polymer has been mixed with between 20% and 70% by weight of an ectoparasiticidal organophosphate active compound.

14. The method as set forth in claim 13, wherein said device includes up to 20% by weight of polyvinyl chloride.

* * * * *

UNITED STATES PATENT AND TRADEMARK OFFICE
CERTIFICATE OF CORRECTION

PATENT NO. : 5,342,619
DATED : August 30, 1994
INVENTOR(S) : Rudolf J. Krzewki and Stanley Ackers It is certified that error appears in the above-indentified patent and that said Letters Patent is hereby corrected as shown below:

Columns 5 and 6 are replaced with Columns 5 and 6 attached hereto.

Column 6, Table III, "Log No." should read -- Lot No. --.

Signed and Sealed this

Seventh Day of February, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT : 5,342,619

DATED : August 30, 1994

INVENTOR(S) : Rudolf J. Krzewki and Stanley Ackers

It is certified that error appears in the above-identified patent and that said Letters Patent is hereby corrected as shown below:

Column 7, Table V should appear as follows:

TABLE V

Efficacy Trials - Control of Horn Flies
Lot 4, Example 1; Lot 2, Example 2

| Location:<br>Treatment Date: | #1<br>5-17-90<br>Average # of Flies<br>per animal | | | #2<br>4-7-90<br>Average # of Flies<br>per animal | | |
|---|---|---|---|---|---|---|
| | Lot 4<br>Ex. 1 | Untagged<br>Control | % Reduction | Lot 2<br>Ex. 2 | Untagged<br>Control | % Reduction |
| # of Animals | 22 | 50. | | 35 | 50 | |
| Pretreatment Count | 268 | 440 | | 800 | 800 | |
| # of Weeks | | | | | | |
| 1 | 22 | 498 | 96 | 90 | 800 | 89 |
| 2 | 14 | 484 | 97 | 150 | 800 | 81 |
| 3 | 4 | 668 | 99 | 100 | 900 | 89 |
| 4 | 5 | 630 | 99 | 20 | 750 | 97 |
| 5 | 9 | 618 | 99 | 12 | 500 | 98 |
| 6 | 4 | 396 | 99 | 10 | 500 | 98 |
| 7 | 3 | 452 | 99 | 10 | 400 | 98 |
| 8 | 6 | 602 | 99 | 6 | 300 | 98 |
| 9 | 30 | 750 | 96 | 10 | 200 | 95 |
| 10 | 26 | 1126 | 98 | 5 | 200 | 98 |
| 11 | 20 | 1166 | 98 | 6 | 200 | 97 |
| 12 | 22 | 1384 | 98 | 7 | 250 | 97 |
| 13 | 48 | 1038 | 95 | — | — | 97 |
| 14 | 64 | 984 | 93 | 20 | 250 | 92 |
| 15 | 38 | 1420 | 97 | 30 | 300 | 90 |
| 16 | 34 | 1106 | 97 | 10 | 300 | 97 |
| 17 | 5 | 706 | 99 | 40 | 300 | 87 |
| 18 | 24 | 594 | 96 | 14 | 350 | 96 |
| 19 | 36 | 610 | 94 | 20 | 300 | 93 |
| 20 | 164 | 540 | 70 | 30 | 300 | 90 |
| 21 | | | | 20 | 300 | 93 |
| 22 | | | | 25 | 300 | 92 |
| 23 | | | | 35 | 300 | 88 |
| 24 | | | | 30 | 200 | 85 |
| 25 | | | | 24 | 250 | 90 |

EXAMPLE 1

Various polymer compositions incorporating Diazinon insecticide were prepared according to the absorption procedure previously described utilizing technical grade (88% purity by weight) Diazinon and quantities within the preferred range. Ear tags were formed from the dry blend by injection molding.

Table I summarizes the composition formulations of the ear tags made according to this example.

TABLE I

Polyurethane Tags Made With Varying Quantities of Resin C and Insecticide

| Lot No. (minimum 200 tags) | Composition, wt. % | | | | | |
|---|---|---|---|---|---|---|
| | 1 | 2 | 3 | 4 | 5 | 6 |
| Resin C | 49.4 | 51.3 | 50.8 | 48.8 | 52.6 | 48.5 |
| Diazinon (88%) | 38.3 | 46.1 | 43.1 | 43.9 | 46.0 | 43.7 |
| PVC | 12.3 | 2.6 | 5.1 | 6.1 | 0 | 6.0 |
| UV and antioxidant Stabilizers (approx. 1:1 by weight) | — | — | — | 0.7 | 0.8 | 1.0 |
| Colorants, Pigments | — | — | 1.0 | 0.5 | 0.6 | 0.8 |
| Average Tag Weight (g) | 14.69 | 14.43 | 14.56 | 14.00 | 15.83 | 13.88 |

Table II provides a summary of the insecticide released during field trials utilizing the tags identified in Table I.

EXAMPLE 2

Various polymer compositions incorporating Diazinon insecticide were prepared according to the absorption procedure using technical grade (88% pure by weight) Diazinon and a dry blend was obtained. Ear tags were formed by injection molding. Table III summarizes the composition formulations of ear tags made according to this example and Table IV provides release rate data on these same tags.

TABLE III

Polyurethane Tags Made With Varying Quantities of Resins B, D, and F and Insecticide

| Log No. (minimum 200 tags) | Composition, wt. % | | | | |
|---|---|---|---|---|---|
| | 1 | 2 | 3 | 4 | 5 |
| Resin D | 53.9 | 42.4 | 51.7 | — | — |
| Resin B | — | — | — | 48.8 | — |
| Resin F | — | — | — | — | 48.4 |
| Diazinon (88%) | 45.8 | 57.3 | 46.5 | 43.9 | 43.5 |
| PVC | — | — | — | 6.1 | 6.0 |
| Stabilizers | — | — | 0.7 | 0.7 | 1.0 |
| Colorants, Pigments | 0.3 | 0.3 | 1.1 | 0.5 | 1.1 |
| Average Tag Weight (g) | 14.28 | 14.31 | 13.64 | 13.87 | 13.85 |

EXAMPLE 3

Ear tags from Lot 4 of Example 1 (Tables I and II) and from Lot 2 of Example 2 (Tables III and IV) were attached to the ears of cattle in herds located in New Mexico and Texas. One tag per animal was used to determine the efficacy against horn flies. In both trials, an untreated cattle herd was located within the vicinity of the tagged herd. On the application day, and weekly thereafter, horn fly counts were taken on at least ten randomly selected tagged and untagged animals. The results are summarized in Table V.

From this data it is evident that a surprising long term efficacy can be achieved with only one tag of the present composition, even under very high fly populations (infestation) for a period of at least six months.

TABLE II

Field Trials
Average Release Rate of Diazinon
For Tags From Table I

| Lot No. | 1 | | 2 | | | 3 | | 4 | | | 5 | 6 |
|---|---|---|---|---|---|---|---|---|---|---|---|---|
| Location | #1 | #2 | #1 | #3 | #2 | #1 | #1 | #4 | #2 | #3 | #1 | #1 |
| Application Date | 1-9-90 | 5-15-90 | 1-20-90 | 3-30-90 | 5-15-90 | 3-30-90 | 3-30-90 | 5-17-90 | 6-27-90 | 7-26-90 | 11-12-90 | 11-15-90 |
| Removal Date | 7-20-90 | 10-11-90 | 7-28-90 | 8-29-90 | 11-26-90 | 9-14-90 | 10-20-90 | 10-3-90 | 10-30-90 | 11-11-90 | 3-30-91 | 4-3-91 |
| Days on Cattle | 191 | 149 | 189 | 151 | 196 | 168 | 204 | 140 | 126 | 108 | 137 | 138 |
| Total Diazinon Released (g) | 2.757 | 3.604 | 4.162 | 4.359 | 4.259 | 4.083 | 3.812 | 3.920 | 3.289 | 2.696 | 3.191 | 2.471 |
| Average Release Rate mg/day | 14.4 | 24.2 | 22.0 | 28.9 | 21.7 | 24.3 | 18.7 | 28.0 | 26.1 | 25.0 | 23.3 | 17.9 |

TABLE IV

Field Trials
Average Release Rate Of Diazinon
For Tags From Table III

| Lot No. | 1 | | | | 2 | | 3 | 4 | | | | 5 |
|---|---|---|---|---|---|---|---|---|---|---|---|---|
| Location | #1 | #1 | #2 | #3 | #3 | #2 | #3 | #2 | #3 | #4 | #2 | #1 |
| Application Date | 3-31-90 | 3-30-90 | 3-23-90 | 5-15-90 | 5-15-90 | 3-27-90 | 6-27-90 | 7-26-90 | 6-27-90 | 5-25-90 | 6-23-90 | 11-10-90 |
| Removal Date | 7-21-90 | 9-15-90 | 8-29-90 | 10-31-90 | 10-1-90 | 8-29-90 | 10-30-90 | 11-11-90 | 10-30-90 | 10-29-90 | 12-01-90 | 4-01-90 |
| Days on Cattle | 112 | 169 | 159 | 168 | 140 | 155 | 126 | 108 | 126 | 157 | 161 | 141 |
| Total Diazinon Released (g) | 2.393 | 3.177 | 3.383 | 3.308 | 4.860 | 4.730 | 2.758 | 2.807 | 3.327 | 4.067 | 4.061 | 2.252 |
| Average Release Rate mg/day | 21.4 | 18.8 | 21.3 | 19.7 | 34.7 | 30.5 | 21.9 | 26.0 | 26.4 | 25.9 | 25.2 | 16.0 |